(12) United States Patent
Kitami et al.

(10) Patent No.: US 7,409,873 B2
(45) Date of Patent: Aug. 12, 2008

(54) CORIOLIS FLOWMETER

(75) Inventors: Hirokazu Kitami, Tokyo (JP); Yuichi Nakao, Tokyo (JP); Norio Sukemura, Tokyo (JP)

(73) Assignee: Oval Corporation, Tokyo (JP)

( * ) Notice: Subject to any disclaimer, the term of this patent is extended or adjusted under 35 U.S.C. 154(b) by 93 days.

(21) Appl. No.: 10/585,819

(22) PCT Filed: Sep. 24, 2004

(86) PCT No.: PCT/JP2004/014439

§ 371 (c)(1),
(2), (4) Date: Oct. 2, 2006

(87) PCT Pub. No.: WO2005/075946

PCT Pub. Date: Aug. 18, 2005

(65) Prior Publication Data

US 2008/0047360 A1    Feb. 28, 2008

(30) Foreign Application Priority Data

Feb. 5, 2004    (JP) .............................. 2004-029630

(51) Int. Cl.
*G01F 1/84* (2006.01)
(52) U.S. Cl. ................................ 73/861.355
(58) Field of Classification Search ............. 73/861.355
See application file for complete search history.

(56) References Cited

U.S. PATENT DOCUMENTS

| | | | | |
|---|---|---|---|---|
| 4,127,028 A | * | 11/1978 | Cox et al. ............... | 73/861.355 |
| 4,730,501 A | * | 3/1988 | Levien ................... | 73/861.357 |
| 4,825,705 A | * | 5/1989 | Hohloch et al. ........ | 73/861.355 |
| 5,020,375 A | * | 6/1991 | Back-Pedersen et al. ..................... | 73/861.355 |
| 5,115,683 A | * | 5/1992 | Pratt ...................... | 73/861.355 |
| 5,343,764 A | * | 9/1994 | Mattar et al. ........... | 73/861.355 |
| 5,357,811 A | * | 10/1994 | Hoang ................... | 73/861.355 |
| 5,551,307 A | * | 9/1996 | Kane et al. ............. | 73/861.356 |
| 5,675,093 A | * | 10/1997 | Young et al. ........... | 73/861.355 |

FOREIGN PATENT DOCUMENTS

| | | |
|---|---|---|
| JP | 04-157328 | 5/1992 |
| JP | 6-7325 | 2/1994 |
| JP | 2654341 | 9/1997 |
| JP | 11-211529 | 8/1999 |

* cited by examiner

*Primary Examiner*—Harshad Patel
(74) *Attorney, Agent, or Firm*—Wenderoth, Lind & Ponack, L.L.P.

(57) ABSTRACT

A first inlet portion, a second inlet portion, a first outlet portion, and a second outlet portion are fixed to a fixing member, and a connecting tube portion is provided between the first outlet portion and the second inlet portion. Further, the first inlet portion and the second inlet portion are fixed so as to be in a non-parallel state such that the distance between the two increases as they depart from the fixing member, and the first outlet portion and the second outlet portion are similarly arranged in a non-parallel state. The first and second inlet portions and the first and second outlet portions are fixed so as to be arranged symmetrically. Further, the first outlet portion, the second inlet portion, and the connecting tube portion are arranged such that their tube axes are in a straight line. Further, the distance between driven portions is made small.

7 Claims, 11 Drawing Sheets

(a) PRIOR ART

BENDING STRESS (b) PRIOR ART

TORSIONAL STRESS

CORIOLIS FLOWMETER

TECHNICAL FIELD

The present invention relates to a Coriolis flowmeter that is used to obtain the mass flow rate and/or density of a measurement fluid detecting a phase difference and/or vibration frequency proportional to Coriolis forces acting on a flow tube.

BACKGROUND ART

In a Coriolis flowmeter, a tube through which a fluid to be measured flows is supported at one end or both ends thereof, and vibration is applied to a portion of the tube around the supporting point in a direction vertical to the flowing direction of the tube (hereinafter, a tube to which vibration is applied is referred to as a flow tube). The Coriolis flowmeter is a mass flowmeter, which utilizes the fact that the Coriolis forces applied to the flow tube when vibration is thus applied thereto, are proportional to a mass flow rate. The Coriolis flowmeter, which is well known, is roughly classified into two types in terms of flow tube structure: a straight tube type and a bent tube type.

In a Coriolis flowmeter of the straight tube type, when vibration is applied to a straight tube, whose both ends are supported, in a direction vertical to the straight-tube center portion axis, a difference in displacement due to the Coriolis forces is generated between the support portions and the central portion of the straight tube, (that is, a phase difference signal is obtained), and, based on this phase difference signal, the mass flow rate is detected. The straight tube type Coriolis flowmeter, thus constructed has a simple, compact, and solid structure. On the other hand, there arises a problem in that it is difficult to achieve high detection sensitivity.

In contrast, the bent tube type Coriolis flowmeter is superior to the straight tube type Coriolis flowmeter from a view point that it allows selection of a shape for effectively obtaining the Coriolis forces. In fact, it is capable of performing mass flow rate detection with high sensitivity. Known examples of the bent tube type Coriolis flowmeter include one equipped with a single flow tube (see, for example, JP 04-55250 A), one equipped with two flow tubes arranged in parallel (see, for example, Japanese Patent 2939242), and one equipped with a single flow tube in a looped state (see, for example, JP 05-69453 A).

Incidentally, as a driving means for driving the flow tube, a combination of a coil and a magnet is generally employed. Regarding the mounting of the coil and the magnet, it is desirable to mount them at positions not offset with respect to the vibrating direction of the flow tube from the viewpoint of minimizing the positional deviation between the coil and the magnet. In view of this, Japanese Patent 2939242 discloses a construction in which two flow tubes arranged in parallel are mounted so as to hold a coil and a magnet between them. Thus, a design is adopted in which the distance between the two flow tubes opposed to each other is at least large enough to enable the coil and the magnet to be held therebetween.

In the case of a Coriolis flowmeter in which two flow tubes respectively exist in planes parallel to each other and which exhibits a large caliber or high flow tube rigidity, it is necessary to enhance the power of the driving means, so that it is necessary to hold a large driving means between the two flow tubes. Thus, a design is adopted in which the distance between the flow tubes is of necessity large even at the fixing end portions constituting the roots of the flow tubes.

However, an increase in the above-mentioned distance at the fixing end portions involves the following problem: it leads to a deficiency in rigidity at the fixing end portions, with the result that vibration leakage is likely to occur (The flow tubes undergo bending vibration to cause vibration leakage).

On the other hand, in the construction as disclosed in JP 05-69453 B, in which a single flow tube is looped, another problem is involved: as shown in FIGS. 11 and 12, it is necessary for a bent tube portion 101 to exist between a first curved tube portion 102 and a second curved tube portion 103. If such a sharp bending is to be effected, the manufacture is rather difficult and, further, there is a problem in terms of the resistance to pressure of the tubes.

SUMMARY OF THE INVENTION

The present invention has been made in view of the above problems in the prior art. It is an object of the present invention to provide a Coriolis flowmeter which involves minimum positional deviation and is not susceptible to vibration leakage, and which is easy to manufacture and provides high durability.

To attain the object of the present invention, according to the present invention, there is provided, as shown in FIG. 1 illustrative of its basic construction, a Coriolis flowmeter 11 including a measurement flow tube 1 including first and second curved tube portions 2 and 3. The first curved tube portion 2 has a first inlet portion 4 through which a measurement fluid flows in and a first outlet portion 5 through which the measurement fluid flows out, while the second curved tube portion 3 has a second inlet portion 6 through which the measurement fluid flows in and a second outlet portion 7 through which the measurement fluid flows out. A fixing member 8 is situated in a middle position of the flow tube 1 as seen in plan view (i.e., when viewed looking down at the flow tube 1), and the first inlet portion 4, the second inlet portion 6, the first outlet portion 5, and the second outlet portion 7 are fixed to the fixing member. The Coriolis flowmeter 11 is used to obtain at least one of a mass flow rate and a density of the measurement fluid through detection of at least one of a phase difference and a vibration frequency proportional to the Coriolis forces acting on the first and second curved tube portions 2 and 3 by vibrating the first and second curved tube portions 2 and 3 with the first and second curved tube portions 2 and 3 being opposed to each other. The first inlet portion 4, the second inlet portion 6, the first outlet portion 5, and the second outlet portion 7 are fixed to the fixing member 8 such that their tube axes are arranged in the same plane, the first inlet portion 4 and the second inlet portion 6 being arranged in a non-parallel state such that a distance therebetween increases with increasing (distance) departure from the fixing member 8; and such that the first outlet portion 5 and the second outlet portion 7 are arranged in a non-parallel state such that a distance therebetween increases with increasing departure (distance) from the fixing member 8. The first and second inlet portions 4 and 6 and the first and second outlet portions 5 and 7 are fixed so as to be arranged symmetrically. A distance between respective driven portions 10 of the first and second curved tube portions 2 and 3 is smaller than a distance between respective portions thereof (connecting portions 16a) continuous with the driven portions 10.

Further, to attain the object of the present invention, there is provided, as shown in FIG. 1, a Coriolis flowmeter 11 including a measurement flow tube 1 including first and second curved tube portions 2 and 3, the first curved tube portion 2 having a first inlet portion 4 through which a measurement fluid flows in and a first outlet portion 5 through which the measurement fluid flows out, the second curved tube portion 3 having a second inlet portion 6 through which the measurement fluid flows in and a second outlet portion 7 through which the measurement fluid flows out. A fixing member 8 is situated in a middle position of the flow tube 1 as seen in plan view, and the first inlet portion 4, the second inlet portion 6, the first outlet portion 5, and the second outlet portion 7 are fixed to the fixing member. A connecting tube portion 9 is provided between the first outlet portion 5 and the second inlet portion 6 and connects the first outlet portion 5 and the second inlet portion 6. The Coriolis flowmeter 11 is used to obtain at least one of a mass flow rate and a density of the measurement fluid through detection of at least one of a phase difference and a vibration frequency proportional to the Coriolis forces acting on the first and second curved tube portions 2 and 3 by vibrating the first and second curved tube portions 2 and 3 with the first and second curved tube portions 2 and 3 being opposed to each other. The first inlet portion 4, the second inlet portion 6, the first outlet portion 5, and the second outlet portion 7 are fixed to the fixing member 8 such that the first inlet portion 4 and the second inlet portion 6 are arranged in a non-parallel state such that a distance therebetween increases with increasing departure from the fixing member 8; and the first outlet portion 5 and the second outlet portion 7 are arranged in a non-parallel state such that a distance therebetween increases with increasing departure from the fixing member 8, the first and second inlet portions 4 and 6 and the first and second outlet portions 5 and 7 being arranged symmetrically. The first outlet portion 5, the second inlet portion 6, and the connecting tube portion 9 are arranged such that their tube axes are in a straight line. A distance between respective driven portions 10 of the first and second curved tube portions 2 and 3 is smaller than a distance between respective portions thereof (connecting portions 16a) continuous with the driven portions 10.

Further, to attain the object of the present invention, in the Coriolis flowmeter, the portions (connecting portions 16a) continuous with the driven portion 10 of the first curved tube portion 2 and the first inlet portion 4 and the first outlet portion 5 are formed and arranged so as to be parallel to each other, and the portions (connecting portions 16a) continuous with the driven portion 10 of the second curved tube portion 3 and the second inlet portion 6 and the second outlet portion 7 are formed and arranged so as to be parallel to each other.

Further, to attain the object of the present invention, in the Coriolis flowmeter, the fixing member 8 is formed substantially in one of a circular configuration and an arcuate configuration in plan view.

Further, to attain the object of the present invention, in the Coriolis flowmeter, the fixing member is formed in a wall-like configuration.

Due to this construction, when the first curved tube portion 2 and the second curved tube portion 3 are vibrated while opposed to each other (In the state shown in FIG. 1, a repulsive action is generated in the driving means; in the case of an attracting action, the directions of the arrows in FIG. 1 are reversed), the fixing member 8, to which the first inlet portion 4, the second inlet portion 6, the first outlet portion 5, and the second outlet portion 7 are fixed, receives at each fixing portion a torsional stress due to a torsional vibration converted from a bending vibration.

However, as shown in FIG. 1, the first inlet portion 4 and the second inlet portion 6 are not parallel to each other, and the first outlet portion 5 and the second outlet portion 7 are not parallel to each other, either. Further, the first and second inlet portions 4 and 6 and the first and second outlet portions 5 and 7 are in symmetrical positional relationships. Thus, when the first curved tube portion 2 and the second curved tube portion 3 are vibrated while opposed to each other, the torsional stress due to the first inlet portion 4 and the second outlet portion 7 is canceled by these two, and the torsional stress due to the second inlet portion 6 and the first outlet portion 5 is also canceled by these two. As a result, substantially no vibration is generated in the fixing member 8, and the loads applied to the first inlet portion 4, the second inlet portion 6, the first outlet portion 5, and the second outlet portion 7 are reduced.

Accordingly, in the present invention, even if the rigidity of the fixing member 8 is low, and if the mass is small, it is possible to effectively restrain vibration leakage. Further, as shown in FIG. 1, the first outlet portion 5, the second inlet portion 6, and the connecting tube portion 9 are arranged continuously in a straight line, so that, according to the present invention, it is possible to enhance the productivity and durability of a Coriolis flowmeter.

Further, the distance between the driven portions 10 is small. Therefore, according to the present invention, it is possible to minimize the positional deviation of the driving means in these driven portions 10.

According to a first aspect of the present invention, it is possible to provide a Coriolis flowmeter which involves minimum positional deviation and which is not subject to vibration leakage.

According to the present invention, it is possible to provide a Coriolis flowmeter which involves minimum positional deviation and is not subject to vibration leakage, and which is easy to manufacture and provides high durability.

According to the present invention, it is possible to provide a Coriolis flowmeter in which the manufacture of the first and second curved tube portions is further facilitated.

According to the present invention, uniform fixation is possible in the flow tube circumferential direction, so that it is possible to provide a Coriolis flowmeter which is still less subject to vibration leakage.

According to the present invention, it is possible to achieve a reduction in the weight and cost of a Coriolis flowmeter.

BRIEF DESCRIPTION OF THE DRAWINGS

FIGS. 3A and 3B are diagrams for comparing conventional Coriolis flowmeters with that of the present invention, of which FIG. 3A shows the type in which the inlet portions and the outlet portions are directed upwards as seen in the drawing, and FIG. 3B shows the type in which the inlet portions and the outlet portions are directed horizontally as seen in the drawing;

FIGS. 4A through 4D are diagrams showing a first embodiment of the present invention, of which FIG. 4A is a main portion front view, FIG. 4B is a sectional view taken along the line A1-A1 of FIG. 4A, FIG. 4C is a sectional view taken along the line B1-B1 of FIG. 4A, and FIG. 4D is a side view of FIG. 4A;

FIGS. 5A through 5D are diagrams showing a second embodiment of the present invention, of which FIG. 5A is a main portion front view, FIG. 5B is a sectional view taken along the line A2-A2 of FIG. 5A, FIG. 5C is a sectional view taken along the line B2-B2 of FIG. 5A, and FIG. 5D is a side view of FIG. 5A;

FIGS. 6A through 6D are diagrams showing a third embodiment of the present invention, of which FIG. 6A is a main portion front view, FIG. 6B is a sectional view taken along the line A3-A3 of FIG. 6A, FIG. 6C is a sectional view taken along the line B3-B3 of FIG. 6A, and FIG. 6D is a side view of FIG. 6A;

FIGS. 7A through 7D are diagrams showing a fourth embodiment of the present invention, of which FIG. 7A is a main portion front view, FIG. 7B is a sectional view taken along the line A4-A4 of FIG. 7A, FIG. 7C is a sectional view taken along the line B4-B4 of FIG. 7A, and FIG. 7D is a side view of FIG. 7A;

FIGS. 8A through 8D are diagrams showing a fifth embodiment of the present invention, of which FIG. 8A is a main portion front view, FIG. 8B is a sectional view taken along the line A5-A5 of FIG. 8A, FIG. 8C is a sectional view taken along the line B5-B5 of FIG. 8A, and FIG. 8D is a side view of FIG. 8A;

FIGS. 9A through 9D are diagrams showing a sixth embodiment of the present invention, of which FIG. 9A is a main portion front view, FIG. 9B is a sectional view taken along the line A6-A6 of FIG. 9A, FIG. 9C is a sectional view taken along the line B6-B6 of FIG. 9A, and FIG. 9D is a side view of FIG. 9A;

FIGS. 10A through 10D are explanatory views showing another example of the fixing member, of which FIG. 10A is a front view of a Coriolis flowmeter, FIG. 10B is a sectional view taken along the line A7-A7 of FIG. 10A, FIG. 10C is a sectional view taken along the line B7-B7 of FIG. 10A, and FIG. 10D is a side view of FIG. 10A;

DETAILED DESCRIPTION OF THE INVENTION

In the following, the present invention will be described with reference to the drawings.

Figure 1:
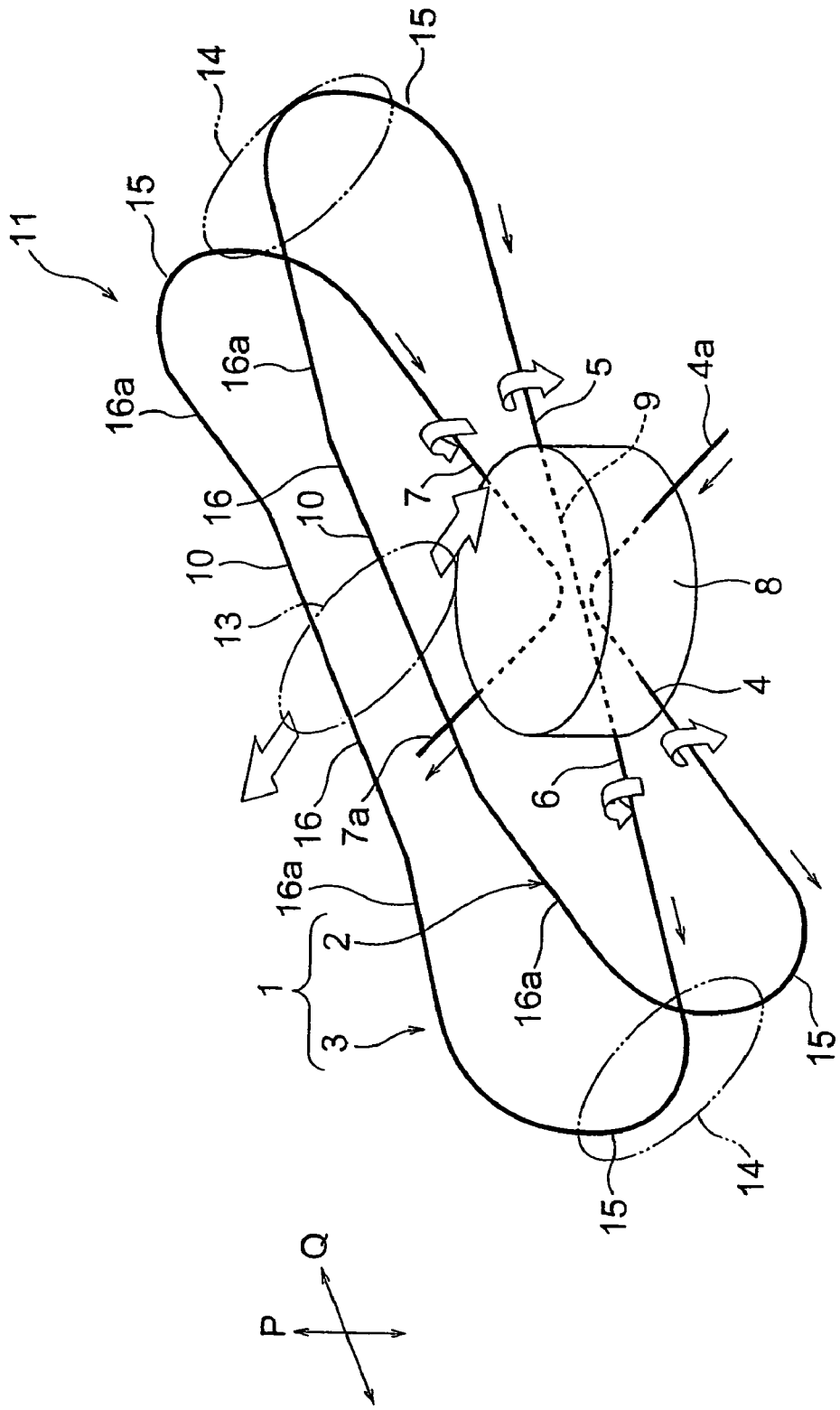
FIG. 1 is a schematic view of a Coriolis flowmeter according to an embodiment of the present invention, showing the basic construction of a main portion of the Coriolis flowmeter.
Figure 2:
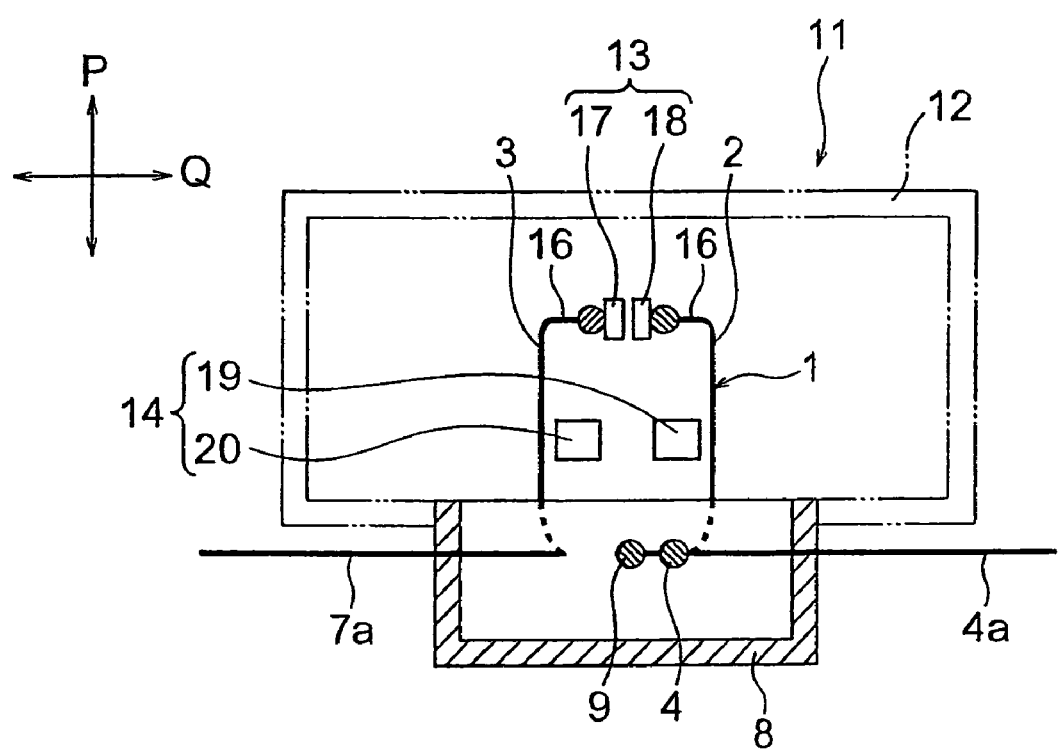
FIG. 2 is a longitudinal sectional view of the central portion (including the casing) of the Coriolis flowmeter of FIG. 1.

FIG. 1 is a schematic view of a Coriolis flowmeter according to an embodiment of the present invention, showing the basic construction of a main portion of the Coriolis flowmeter. FIG. 2 is a longitudinal sectional view of the central portion (including the casing) of the Coriolis flowmeter of FIG. 1.

In FIGS. 1 and 2, a Coriolis flowmeter 11 according to the present invention includes a casing 12, a single flow tube 1 accommodated in the casing 12, a drive device 13, a sensor portion (not shown) having a pair of vibration detecting sensors 14 and a temperature sensor (not shown), a signal computation processing portion (not shown) for performing computation processing on mass flow rate, etc. based on a signal from the sensor portion, and an excitation circuit portion (not shown) for exciting the drive device 13. In the following, these components will be described.

The casing 12 has a structure resistant to bending and torsion. Further, the casing 12 is formed in a size large enough to accommodate the flow tube 1, with a fixing member 8 for fixing the flow tube 1 in position being mounted to the casing 12. Further, the casing 12 is formed so as to be capable of protecting the main portion of the flowmeter including the flow tube 1. The casing 12 is filled with an inert gas, such as argon gas. Due to the filling with the inert gas, condensation on the flow tube 1, etc. is prevented.

The casing 12 is mounted to the fixing member 8 by an appropriate means. The fixing member 8 is formed in a circular configuration in plan view. Although desirable, it is not always necessary for the fixing member 8 to be of a circular configuration in plan view. For example, it may be formed as a fixing member of a rectangular configuration in plan view or, as shown in FIGS. 10A through 10D, it may be formed as arcuate fixing members 8″ of a Coriolis flowmeter 1″. Further, in this embodiment, the fixing member 8 is formed as a wall member defining an inner space.

The flow tube 1 consists of a single looped measurement conduit (It is not always necessary for the flow tube 1 to consist of a single looped conduit, as described in detail below with reference to a sixth embodiment of the present invention), and includes a first curved tube portion 2 and a second curved tube portion 3 arranged so as to be opposed to each other, and a connecting tube portion 9 connecting the first curved tube portion 2 and the second curved tube portion 3 to each other. Assuming that the arrow line P and the arrow line Q in FIG. 1 respectively indicate the vertical direction and the horizontal direction, the first curved tube portion 2 and the second curved tube portion 3 are formed substantially in an elliptical configuration, with both being elongated in the horizontal direction.

The first curved tube portion 2 has a first inlet portion 4 through which measurement fluid flows in and a first outlet portion 5 through which measurement fluid flows out. The second curved tube portion 3 has a second inlet portion 6 through which measurement fluid flows in and a second outlet portion 7 through which measurement fluid flows out. The connecting tube portion 9 is provided between the first outlet portion 5 and the second inlet portion 6. In other words, the connecting tube portion 9 is provided for the purpose of connecting the first outlet portion 5 and the second inlet portion 6 to each other. The first outlet portion 5, the second inlet portion 6, and the connecting tube portion 9 are formed and arranged such that they are continuously connected together in a straight line, in other words, that the axes of the three tubes are in a straight line.

The first inlet portion 4, the second inlet portion 6, the first outlet portion 5, and the second outlet portion 7 are fixed to the fixing member 8. The first inlet portion 4 and the second inlet portion 6 are fixed and arranged in a non-parallel state such that the distance between them increases as they depart from the fixing member 8. Similarly, the first outlet portion 5 and the second outlet portion 7 are fixed and arranged in a non-parallel state such that the distance between them increases as they depart from the fixing member 8. Further, the first and second inlet portions 4 and 6 and the first and second outlet portions 5 and 7 are fixed and arranged so as to be in symmetrical positional relationships.

Here, as can be seen from the drawings, the first inlet portion 4, the second inlet portion 6, the first outlet portion 5, and the second outlet portion 7 are fixed to the fixing member 8 so as to be in the same plane. However, the way the first inlet portion 4, the second inlet portion 6, the first outlet portion 5, and the second outlet portion 7 are fixed to the fixing member 8 is not restricted to this. For example, the fixation to the fixing member 8 may also be effected such that the first inlet portion 4 and the second outlet portion 7 are in the same plane and that the first outlet portion 5 and the second inlet portion 6 are in the same plane.

A terminal 4a of the first inlet portion 4 is led to the exterior in order to allow inflow of measurement fluid. Further, like the terminal 4a, the terminal 7a of the second outlet portion 7 is led to the exterior in order to allow outflow of measurement fluid. The terminal 4a and the terminal 7a are led out so as to be perpendicular to the arrow line P of FIG. 1 and so as to extend in opposite directions. Measurement fluid flowing in through the terminal 4a of the first curved tube portion 4 passes through the first curved tube portion 2, the connecting tube portion 9, and the second curved tube portion 3 before flowing out through the terminal 7a of the second outlet portion 7 (As for the flow of the measurement fluid, see the arrows in FIG. 1).

The first curved tube portion 2 has, in addition to the first inlet portion 4 and the first outlet portion 5, substantially arcuate curved portions 15 and a straight apex portion 16. Similarly, the second curved tube portion 3 has, in addition to the second inlet portion 6 and the second outlet portion 7, substantially arcuate curved portions 15 and another straight apex portion 16. The apex portions 16 are formed in a substantially U-shaped configuration so as to be back to back in plan view. That is, formed in each apex portion 16 are a driven portion 10 and connecting portions 16a. The connecting portions 16a are formed on either side of the driven portion 10. The connecting portions 16a are formed as portions connecting the driven portion 10 with the curved portions 15. The driven portions 10 are formed and arranged such that the distance between them is smaller than the distance between the curved portions 15.

The connecting portions 16a of the first curved tube portion 2 are formed so as to be parallel to the first inlet portion 4 and the first outlet portion 5. Similarly, the connecting portions 16a of the second curved tube portion 3 are formed so as to be parallel to the second inlet portion 6 and the second outlet portion 7. It goes without saying that this formation helps to facilitate the production of the curved portion 15.

The driven portion 10 of the first curved tube portion 2 and the driven portion 10 of the second curved tube portion 3 are arranged in parallel with a gap therebetween large enough to hold a relative small driving device 13. Similarly, the curved portions 15 of the first curved tube portion 2 and the curved portions 15 of the second curved tube portion 3 are arranged with a gap therebetween large enough to hold the vibration detecting sensors 14. The first inlet portion 4 and the second inlet portion 6 are formed and arranged such that the distance therebetween is large at the position corresponding to the curved portions 15 and that the distance therebetween is small at the position corresponding to the fixing member 8. Similarly, the first outlet portion 5 and the second outlet portion 7 are formed and arranged such that the distance therebetween is large at the position corresponding to the curved portions 15 and that the distance therebetween is small at the position corresponding to the fixing member 8.

Since the distance between the first inlet portion 4 and the second inlet portion 6 is small at the fixing member 8, vibration leakage does not easily occur. Further, as described below, a structure is adopted which cancels torsional stress. Substantially no vibration is generated in the fixing member 8. Further, since the distance between the driven portions 10 is small, the positional deviation generated in the driving device 13 is minimum. Further, also in the vibration detecting sensors 14, the positional deviation is minimum.

The material of the flow tube 1 is one usually adopted in this technical field, such as stainless steel, hastelloy, or titanium alloy.

The driving device 13 constituting the sensor portion causes the first curved tube portion 2 and the second curved tube portion 3 to vibrate while opposed to each other, and is equipped with a coil 17 and a magnet 18. The driving device 13 is arranged at the center of the driven portions 10 and so as to be held between them. In other words, the driving device 13 is mounted at a position not offset with respect to the vibrating direction of the flow tube 1.

The coil 17 of the driving device 13 is mounted to one driven portion 10 of the flow tube 1 by using a dedicated mounting tool. Further, although not particularly shown, an FPC (flexible printed circuit) or electric wire is led out from the coil 17. The magnet 18 of the driving device 13 is mounted to the other driven portion 10 of the flow tube 1 by using a dedicated mounting tool.

When an attracting action is generated in the driving device 13, the magnet 18 is inserted into the coil 17, with the result that the driven portions 10 of the flow tube 1 are brought close to each other. In contrast, when a repulsive action is generated, the driven portions 10 of the flow tube 1 are moved away from each other. Since the flow tube 1 is fixed to the fixing member 8 as described above, the driving device 13 alternately drives the flow tube 1 in the rotating direction around the fixing member 8.

The vibration detecting sensors 14 constituting the sensor portion are sensors for detecting vibration of the flow tube 1 and for detecting a phase difference proportional to the Coriolis forces acting on the flow tube 1, and are each equipped with a coil 19 and a magnet 20 (The sensors are not restricted to the ones as described above; they may also be acceleration sensors, optical means, or capacitance type or distortion type (piezoelectric type) means as long as they are capable of detecting one of displacement, velocity, and acceleration).

The vibration detecting sensors 14 thus constructed are arranged, for example, at positions within a range where they are held between the curved portions 15 of the flow tube 1 and where they can detect the phase difference proportional to the Coriolis force.

The respective coils 19 of the vibration detecting sensors 14 are mounted to one curved portion 15 of the flow tube 1 by using a dedicated mounting tool. Further, although not particularly shown, FPCs (flexible printed circuits) or electric wires are led out from the coils 19. The respective magnets 20 of the vibration detecting sensors 14 are mounted to the other curved portion 15 of the flow tube 1 by using a dedicated mounting tool.

Although not particularly shown, aboard or the like is provided inside the Coriolis flowmeter 11 of the present invention. Further, connected to the board is a wire harness led out to the exterior of the casing 12.

The temperature sensor constituting a part of the sensor portion serves to effect temperature compensation on the Coriolis flowmeter 11, and is mounted to the flow tube 1 by an appropriate means. More specifically, it is mounted, for example, to the first inlet portion 4. Further, an FPC (flexible printed circuit) or electric wire (not shown), led out from the temperature sensor, is connected to the board.

Wiring and connection are effected in the signal computation processing portion such that there are input thereto a detection signal from one vibration detecting sensor 14 regarding deformation of the flow tube 1, a detection signal from the other vibration detecting sensor 14 regarding deformation of the flow tube 1, and a detection signal from the temperature sensor regarding the temperature of the flow tube 1. In this signal computation processing portion, computation on mass flow rate and density is effected based on the detection signals input from the sensor portion. Further, in the signal computation processing portion, the mass flow rate and density obtained through computation are displayed on a display (not shown).

The excitation circuit portion includes a smoothing portion, a comparing portion, a target setting portion, a variable amplification portion, and a drive output portion. Wiring is effected in the smoothing portion so that a detection signal from one vibration detecting sensor 14 (or the other vibration detecting sensor 14) may be extracted. Further, the smoothing portion has a function by which it can rectify and smooth the input detection signal and output a DC voltage proportional to the amplitude thereof. The comparing portion has a function by which it can compare the DC voltage from the smoothing portion with a target set voltage output from the target setting portion and control the gain of the variable amplification portion to control the amplitude of the resonance vibration in conformity with the target set voltage.

In the above construction, when measurement fluid is caused to flow through the flow tube 1, and the driving device 13 is driven to cause the first curved tube portion 2 and the second curved tube portion 3 to vibrate while opposed to each other, due to a difference in phase generated by the Coriolis force at the vibration detecting sensors 14, the mass flow rate is calculated by the signal computation processing portion. Further, in this embodiment, the density is also calculated from the vibration frequency.

Figure 3:
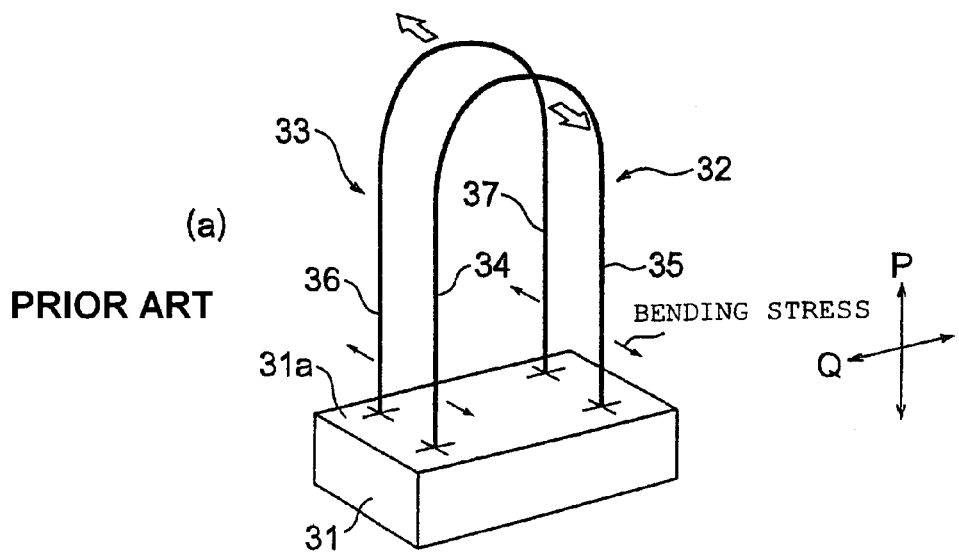
Figure 3:
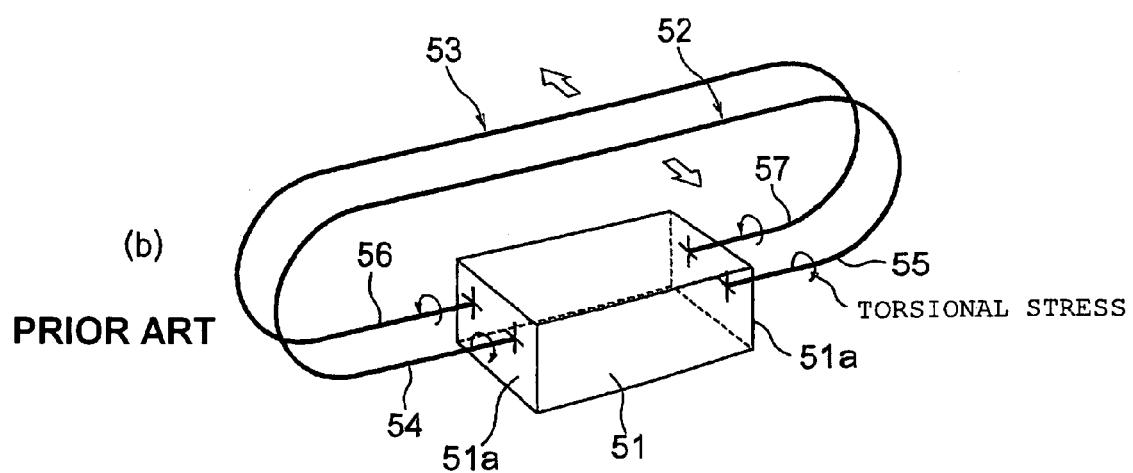
Figure 4:
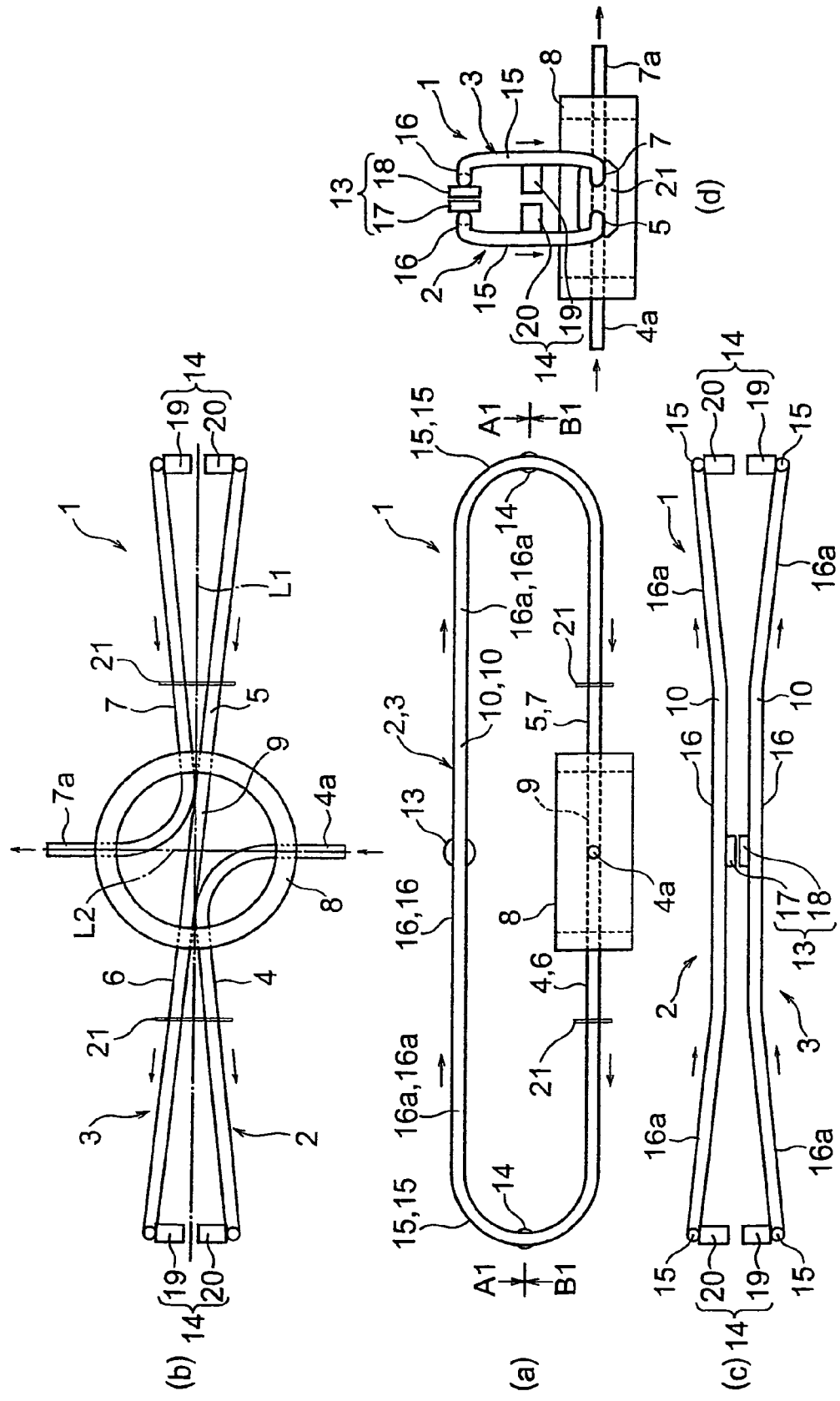
Figure 5:
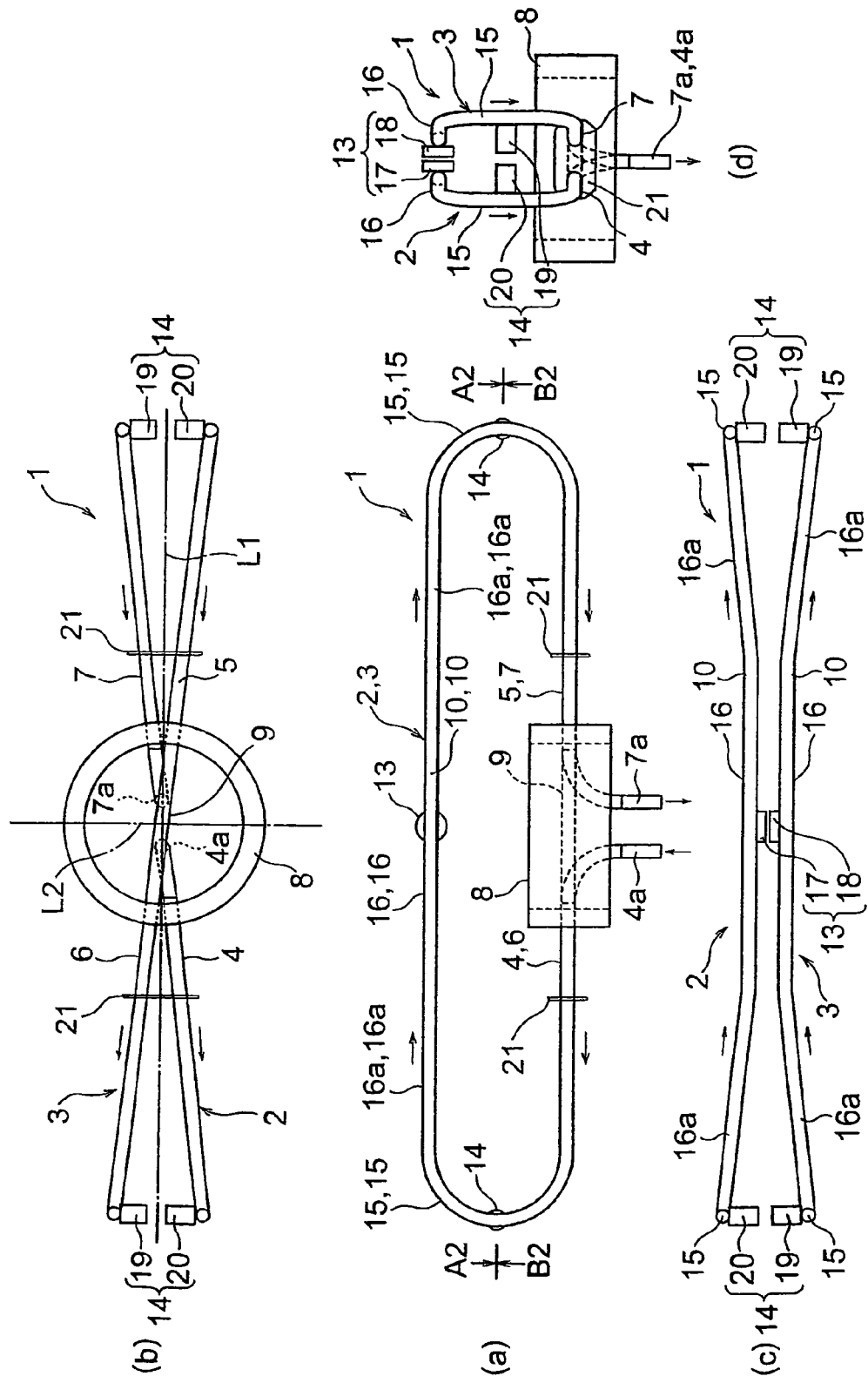
Figure 6:
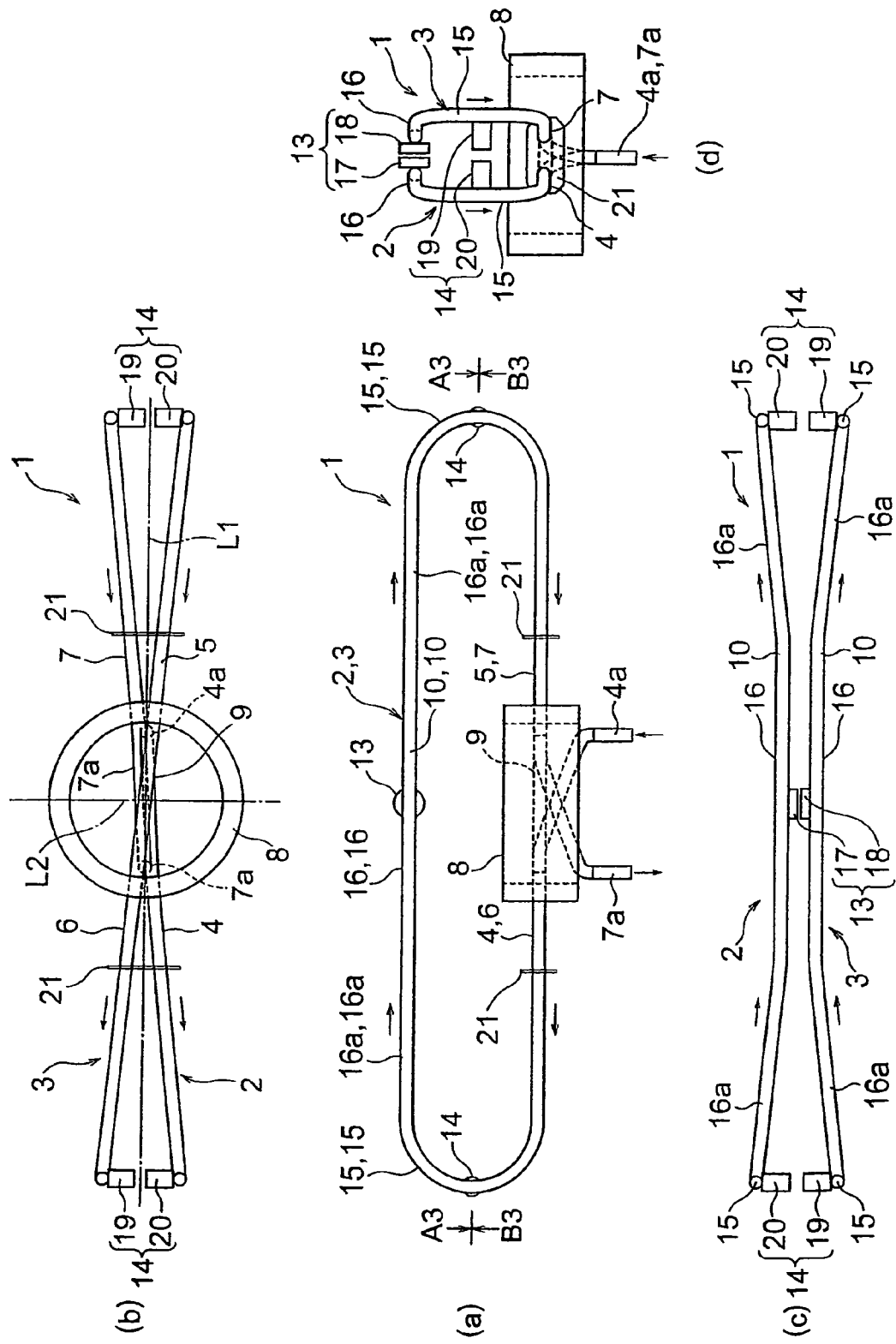
Figure 7:
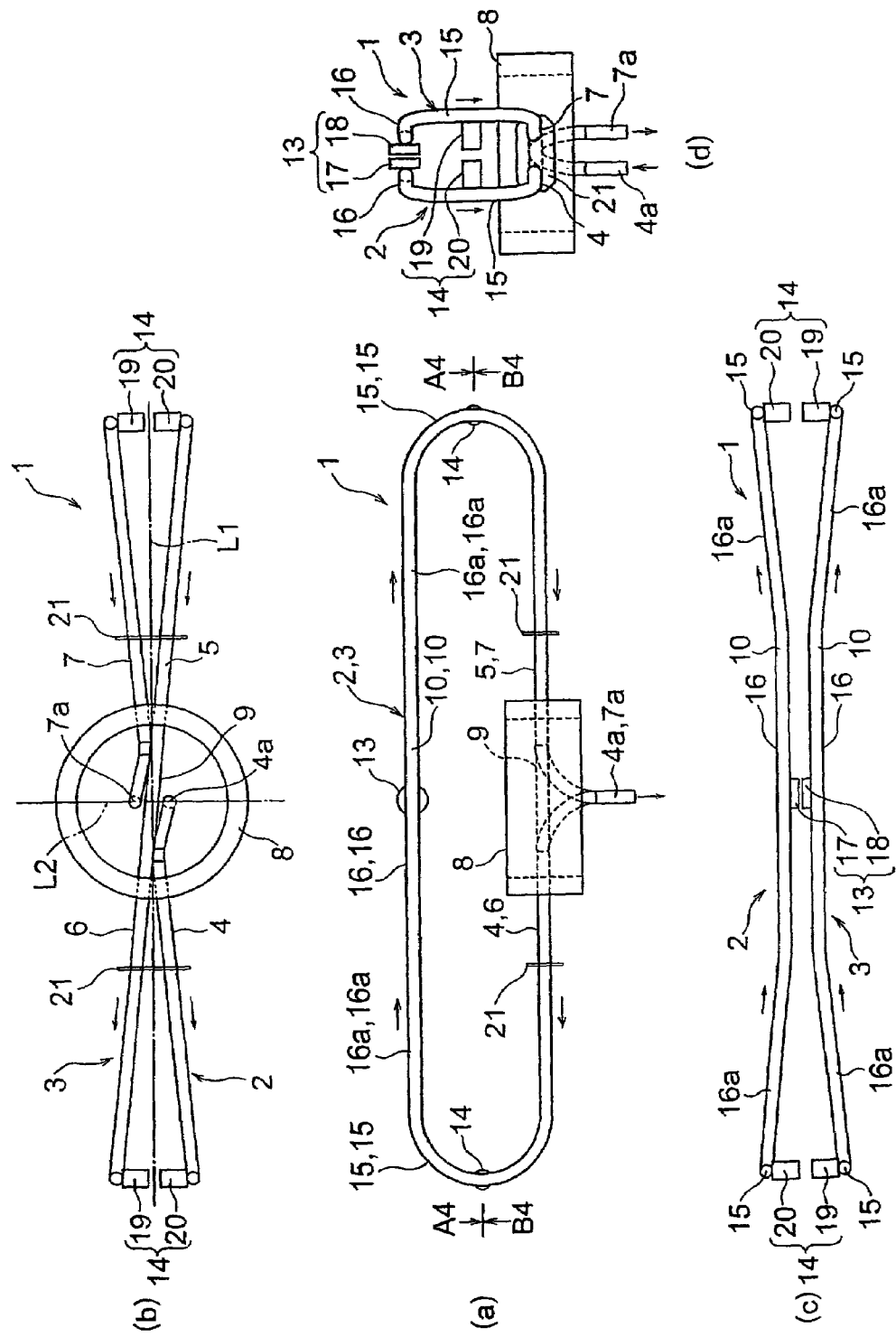
Figure 8:
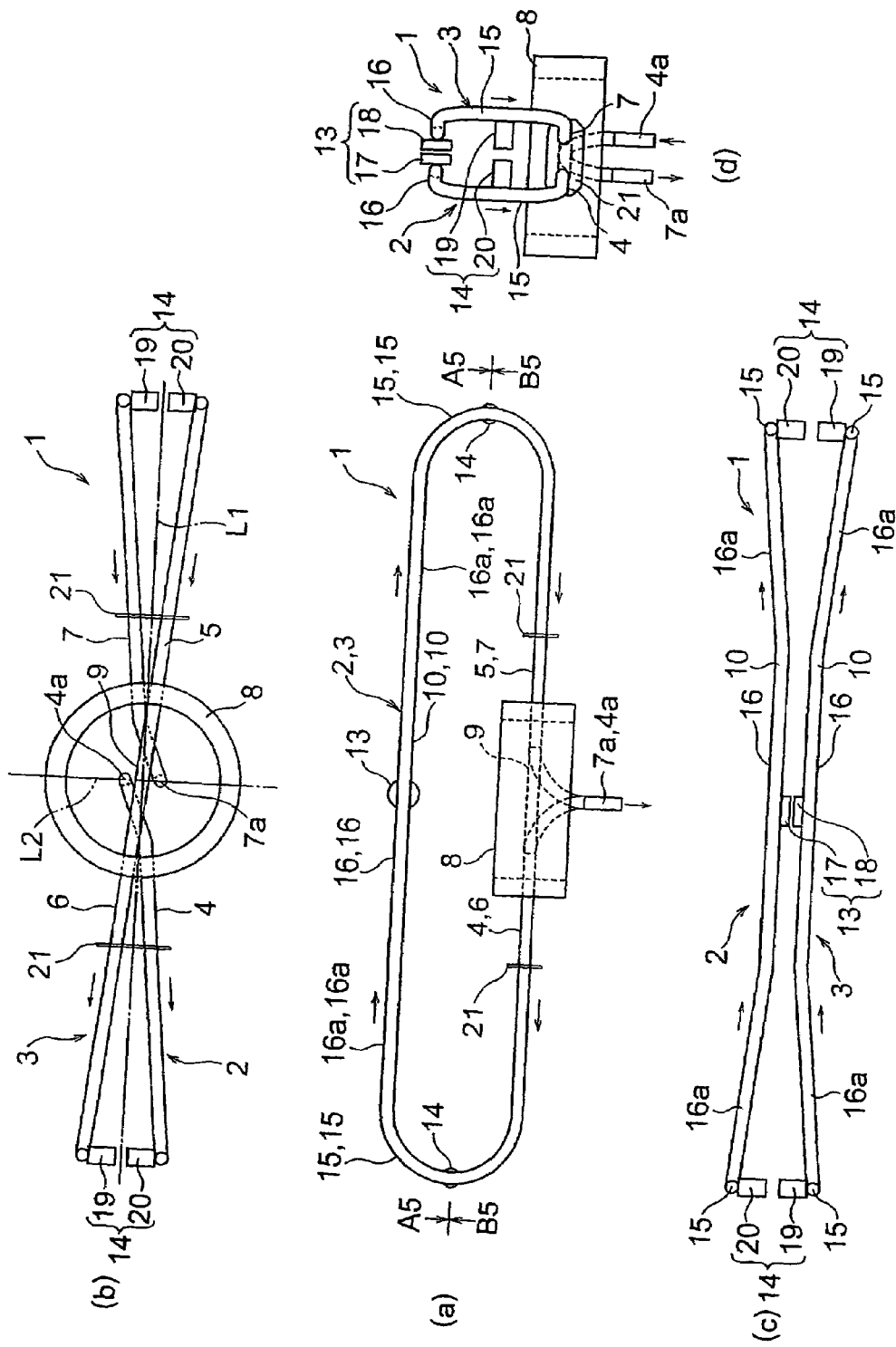
Figure 9:
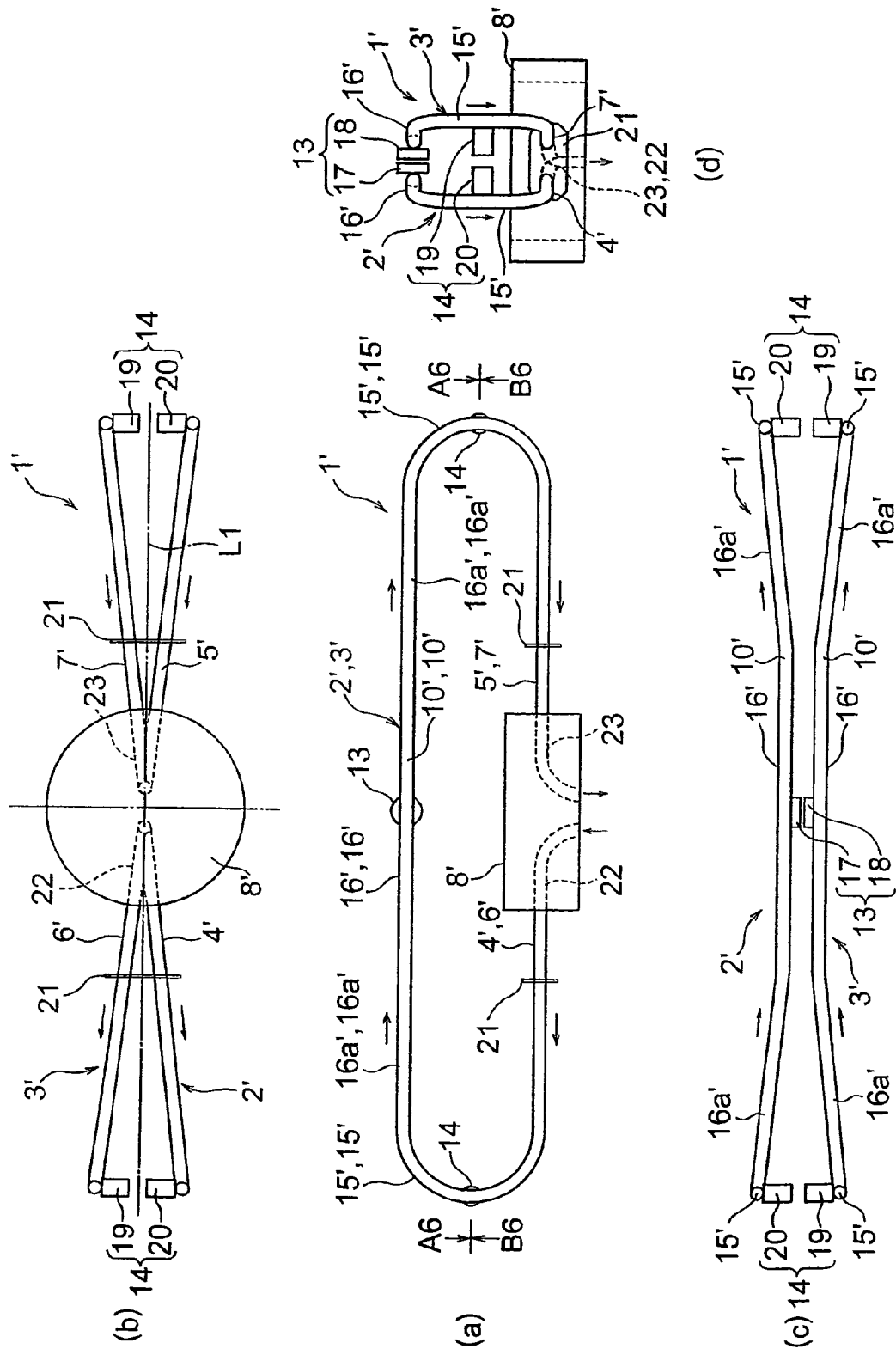
Figure 10:
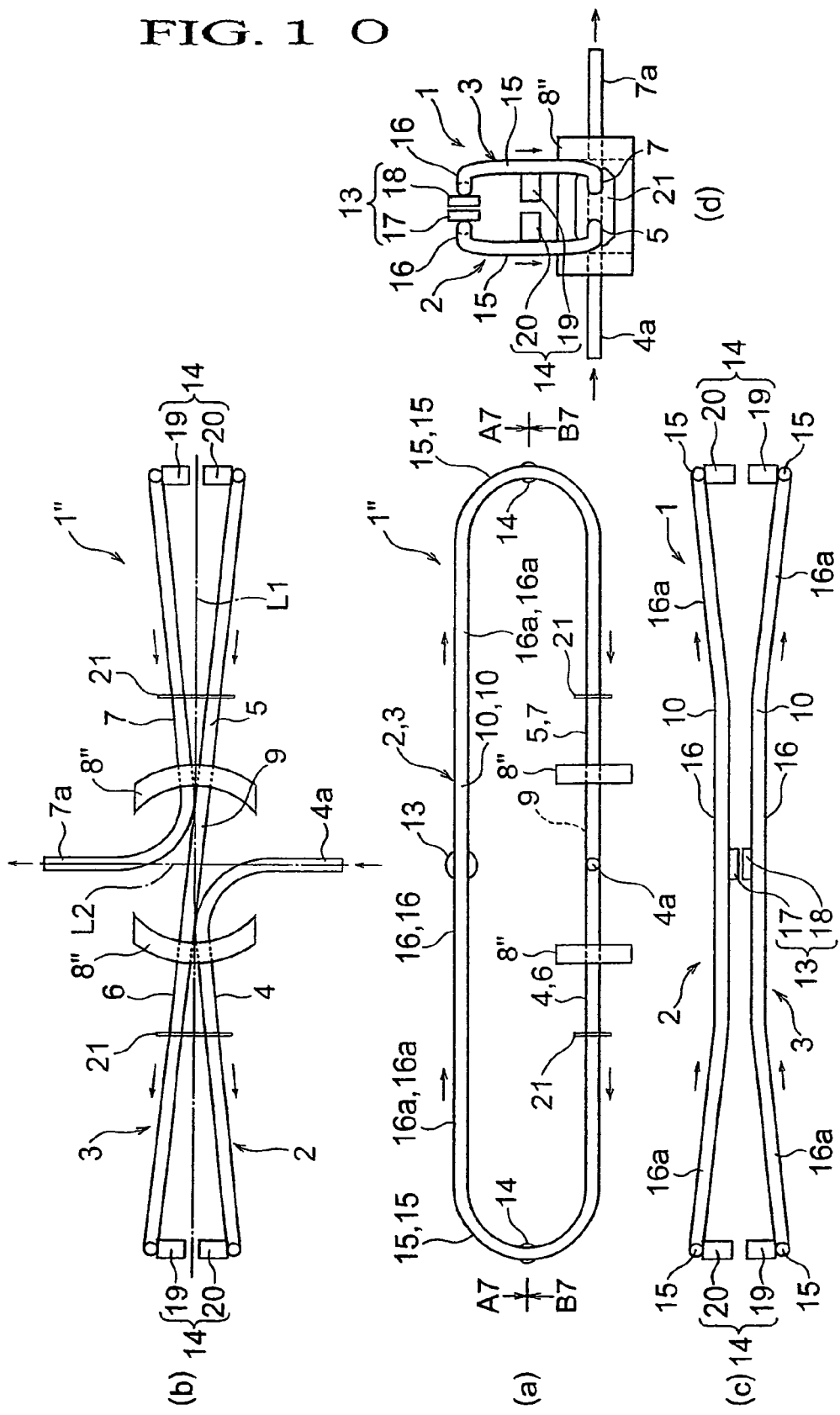
Figure 11:
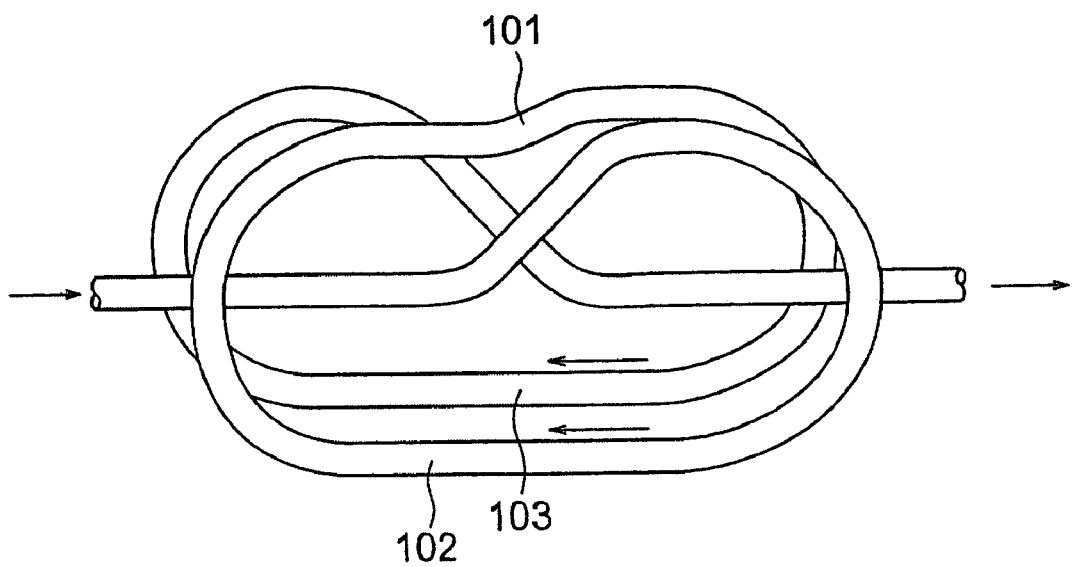
FIG. 11 is a perspective view of the flow tubes of a conventional Coriolis flowmeter.
Figure 12:
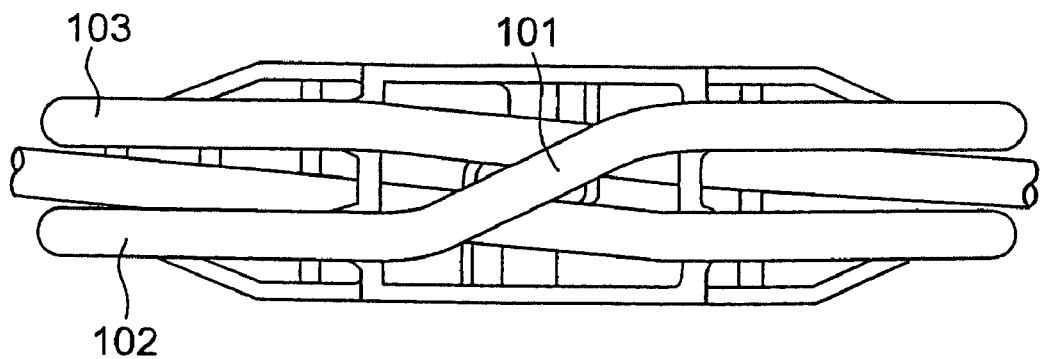
FIG. 12 is a plan view of the flow tubes of FIG. 11.

Here, the superiority of the Coriolis flowmeter 11 of the present invention to the conventional ones as shown in FIGS. 3A and 3B will be clarified. In FIGS. 3A and 3B, the arrow line P indicates the vertical direction, and the arrow line Q indicates the horizontal direction.

In FIG. 3A, fixed to a fixing member 31 are a first curved tube portion 32 and a second curved tube portion 33 constituting a flow tube. The first curved tube portion 32 and the second curved tube portion 33 are both formed in a reverse-U-shaped configuration and are arranged so as to be opposed to each other. The plane as defined by the first curved tube portion 32 and the plane as defined by the second curved tube portion 33 are parallel to each other. Formed in the first curved tube portion 32 are a first inlet portion 34 through which measurement fluid flows in and a first outlet portion 35 through which measurement fluid flow out. Formed in the second curved tube portion 33 are a second inlet portion 36 through which measurement fluid flows in and a second outlet portion 37 through which measurement fluid flows out. The first inlet portion 34, the first outlet portion 35, the second inlet portion 36, and the second outlet portion 37 extend in the vertical direction, and are secured to an upper surface 31a of the fixing member 31 so as to be perpendicular thereto.

When, in the above construction, driving is effected between the apex portions of the first curved tube portion 32 and the second curved tube portion 33 to cause the first curved tube portion 32 and the second curved tube portion 33 to vibrate while opposed to each other (FIG. 3A shows a state in which a repulsive action of the driving device is generated; in the case of an attracting action, the arrows are reversed; this also applies to FIG. 3B), bending stresses as indicated by the arrows in FIG. 3A are generated. The bending stresses have the effect of causing the fixing portions of the first inlet portion 34, the first outlet portion 35, the second inlet portion 36, and the second outlet portion 37 to vibrate in the vertical direction. When the distance between the first inlet portion 34 and the second inlet portion 36 and the distance between the first outlet portion 35 and the second outlet portion 37 are relatively large, there is a fear of vibration leakage occurring due to the above-mentioned vibration in the vertical direction.

In FIG. 3B, fixed to a fixing member 51 are a first curved tube portion 52 and a second curved tube portion 53 constituting a flow tube. The first curved tube portion 52 and the second curved tube portion 53 are both formed as ellipses extending in the horizontal direction and arranged so as to be opposed to each other. The plane as defined by the first curved tube portion 52 and the plane as defined by the second curved tube portion 53 are parallel to each other. The first curved tube portion 52 has a first inlet portion 54 through which measurement fluid flows in and a first outlet portion 55 through which measurement fluid flows out. The second curved tube portion 53 has a second inlet portion 56 through which measurement fluid flows in and a second outlet portion 57 through which measurement fluid flows out. The first inlet portion 54, the first outlet portion 55, the second inlet portion 56, and the second outlet portion 57 extend in the horizontal direction, and are fixed to side surfaces 51a of the fixing member 51 so as to be perpendicular thereto.

In the above construction, when driving is effected between the apex portions of the first curved tube portion 52 and the second curved tube portion 53 to cause the first curved tube portion 52 and the second curved tube portion 53 to vibrate while opposed to each other, torsional stresses as indicated by the arrows in FIG. 3B are generated. In the type as shown in FIG. 3B, bending vibration is converted to torsional vibration, with the result that torsional stress is generated. Thus, it is to be assumed that there occurs no vibration leakage due to the vertical vibration as mentioned above. However, the torsional stress due to the first inlet portion 54 and the torsional stress due to the first outlet portion 55 are torsional stresses in the same direction, and, further, the torsional stress due to the second inlet portion 56 and the torsional stress due to the second outlet portion 57 are torsional stresses in the same direction, so that there is a fear of curving deflection being generated in the fixing member 51.

Referring again to FIG. 1, when the first curved tube portion 2 and the second curved tube portion 3 of the Coriolis flowmeter 11 of the present invention are vibrated while opposed to each other (FIG. 1 shows a state in which the repulsive action of the driving device 13 is generated; in the case of the attracting action, the arrows in FIG. 1 are reversed), there are applied, to the fixing member 8 to which the first inlet portion 4, the second inlet portion 6, the first outlet portion 5, and the second outlet portion 7 are fixed, torsional stresses due to the torsional vibration converted from the bending vibration at each fixing portion. However, as shown in FIG. 1, the first inlet portion 4 and the second inlet portion 6 are not parallel to each other, and the first outlet portion 5 and the second outlet portion 7 are not parallel to each other, either; further, the first and second inlet portions 4 and 6 and the first and second outlet portions 5 and 7 are in symmetrical positional relationships, so that the torsional stresses due to the first inlet portion 4 and the second outlet portion 7 are canceled therebetween, and the torsional stresses due to the second inlet portion 6 and the first outlet portion 5 are also canceled therebetween. Thus, substantially no vibration is generated in the fixing member 8.

According to the present invention, the load on the first inlet portion 4, the second inlet portion 6, the first outlet portion 5, and the second outlet portion 7 is small. Even if the rigidity of the fixing member 8 is low, or if the mass is small, it is possible to effectively restrain vibration leakage. Further, as shown in FIG. 1, the first outlet portion 5, the second inlet portion 6, and the connecting tube portion 9 are arranged continuously in a straight line, so that, according to the present invention, it is possible to enhance the ease of manufacture and durability of a Coriolis flowmeter. In addition, since the distance between the driven portions 10 is small, it is possible to minimize deviation in the positional relationship between the driven portions 10 and the driving device 13.

As described above, according to the present invention, it is possible to provide a Coriolis flow member 11 in which the positional deviation of at least the driving device 13 is minimum, which has little vibration leakage, and which is easy to manufacture and of high durability.

Next, more specific examples of the configuration of the main portion of the Coriolis flowmeter will be described with reference to FIGS. 4A through 9D.

EXAMPLE 1

In FIGS. 4A through 4D, the flow tube 1 is obtained by looping a single measurement flow tube, and includes the first curved tube portion 2 and the second curved tube portion 3 arranged so as to be opposed to each other, and the connecting tube portion 9 connecting the first curved tube portion 2 and the second curved tube portion 3 to each other. In the flow tube 1 shown in FIGS. 4A through 4D, the flow tube 1 as described, for example, with reference to FIG. 1 is embodied. In the following, its construction will be briefly described.

The first curved tube portion 2 has the first inlet portion 4 and the first outlet portion 5. The second curved tube portion 3 has the second inlet portion 6 and the second outlet portion 7. The connecting tube portion 9 is provided between the first outlet portion 5 and the second outlet portion 6. The first outlet portion 5, the second inlet portion 6, and the connecting tube portion 9 are formed and arranged so as to be continuous in a straight line.

The first inlet portion 4 and the second inlet portion 6 are fixed to the fixing member 8 so as to be in the same plane; the first inlet portion 4 and the second inlet portion 6 are arranged so as not to be parallel to each other. Like the first inlet portion 4 and the second inlet portion 6, the first outlet portion 5 and the second outlet portion 7 are fixed to the fixing member 8 so as to be in the same plane, with the first outlet portion 5 and the second outlet portion 7 being arranged so as not to be parallel to each other. The terminal 4a of the first inlet portion 4 and the terminal 7a of the second outlet portion 7 are led out such that, as shown in FIG. 4A, they are perpendicular to the arrow P of FIG. 1 and that the direction in which the measurement fluid flows in (terminal 4a) and the direction in which the measurement fluid flows out (terminal 7a) are opposite to each other.

The driving device 13 is provided between the respective apex portions 16 of the first curved tube portion 2 and the second curved tube portion 3, that is, between the driven portions 10. Further, between the respective curved portions 15 of the first curved tube portion 2 and the second curved tube portion 3, there are provided the vibration detecting sensors 14. A well-known brace bar 21 is provided so as to be astride the first inlet portion 4 and the second inlet portion 6. Similarly, another well-known brace bar 21 is provided so as to be astride the first outlet portion 5 and the second outlet portion 7. The brace bars 21 are spaced apart from the fixing member 8 by a predetermined distance. The arrows in the drawings show how the measurement fluid flows.

EXAMPLE 2

In the flow tube 1 shown in FIGS. 5A through 5D, the lead-out directions of the terminal 4a of the first inlet portion 4 and the terminal 7a of the second outlet portion 7 of the flow tube 1 shown in FIGS. 4A through 4D are changed. In the example shown in FIGS. 5A through 5D, the terminal 4a of the first inlet portion 4 and the terminal 7a of the second outlet portion 7 are led out such that, as shown in FIG. 5A, the direction in which the measurement fluid flows in (terminal 4a) and the direction in which the measurement fluid flows out (terminal 7a) are the same (the vertical direction as indicated by the arrow P of FIG. 1). Further, the terminal 4a of the first inlet portion 4 and the terminal 7a of the second outlet portion 7 are led out so as to be arranged in the center line L1 of the first curved tube portion 2 and the second curved tube portion 3 as shown in FIG. 5B.

EXAMPLE 3

In the flow tube 1 shown in FIGS. 6A through 6D, the lead-out directions of the terminal 4a of the first inlet portion 4 and the terminal 7a of the second outlet portion 7 of the flow tube 1 shown in FIGS. 4A through 4D are changed. In the example shown in FIGS. 6A through 6D, the terminal 4a of the first inlet portion 4 and the terminal 7a of the second outlet portion 7 are led out such that, as shown in FIG. 6A, the direction in which the measurement fluid flows in (terminal 4a) and the direction in which the measurement fluid flows out (terminal 7a) are the same (the vertical direction as indicated by the arrow P of FIG. 1). Further, the first curved tube portion 2 with the terminal 4a of the first inlet portion 4 and the second curved tube portion 3 with the terminal 7a of the second outlet portion 7 cross each other as shown in FIG. 6A, and, in this state, they are led out so as to be arranged in the center line L1 of the first curved tube portion 2 and the second curved tube portion 3 as shown in FIG. 6B.

EXAMPLE 4

In the flow tube 1 shown in FIGS. 7A through 7D, the lead-out directions of the terminal 4a of the first inlet portion 4 and the terminal 7a of the second outlet portion 7 of the flow tube 1 shown in FIGS. 4A through 4D are changed. In the example shown in FIGS. 7A through 7D, the terminal 4a of the first inlet portion 4 and the terminal 7a of the second outlet portion 7 are led out such that, as shown in FIG. 7A, the direction in which the measurement fluid flows in (terminal 4a) and the direction in which the measurement fluid flows out (terminal 7a) are the same (the vertical direction as indicated by the arrow P of FIG. 1). Further, the first curved tube portion 2 with the terminal 4a of the first inlet portion 4 and the second curved tube portion 3 with the terminal 7a of the second outlet portion 7 are led out so as to be arranged, while undergoing bending as shown in FIG. 7B, in the center line L2 perpendicular to the center line L1 of the first curved tube portion 2 and the second curved tube portion 3 as shown in FIG. 7B.

EXAMPLE 5

In the flow tube 1 shown in FIGS. 8A through 8D, the bending directions of the terminal 4a of the first inlet portion 4 and the terminal 7a of the second outlet portion 7 of the flow tube 1 shown in FIGS. 7A through 7D are changed.

EXAMPLE 6

In FIGS. 9A through 9D, a flow tube 1' includes two tube portions consisting of a first curved tube portion 2' and a second curved tube portion 3. The first curved tube portion 2' has a first inlet portion 4' and a first outlet portion 5'. The second curved tube portion 3' has a second inlet portion 6' and a second outlet portion 7'.

The first inlet portion 4' and the second inlet portion 6' are fixed to a manifold 22 of the fixing member 8' so as to be in the same plane with the first inlet portion 4' and the second inlet portion 6' being arranged so as not to be parallel to each other. Like the first inlet portion 4' and the second inlet portion 6', the first outlet portion 5' and the second outlet portion 7' are fixed to the manifold 22 of the fixing member 8' so as to be in the same plane, with the first outlet portion 5' and the second outlet portion 7' being arranged so as not to be parallel to each other. The measurement fluid flows into the manifold 22 of the fixing member 8'. Further, the measurement fluid flows out through a manifold 23 of the fixing member 8'.

In the flow tubes 1 shown in FIGS. 4A through 10D, the driving device 13 is provided between the apex portions 16, 16' of the first curved tube portion 2, 2' and the second curved tube portion 3, 3', that is, between the driven portions 10, 10'.

Further, the vibration detecting sensors 14 are provided between the curved portions 15, 15' of the first curved tube portion 2, 2' and the second curved tube portion 3, 3'. The brace bar 21 is provided to the first inlet portion 4, 4' and the second inlet portion 6, 6' so as to be astride the first inlet portion 4, 4' and the second inlet portion 6, 6'. Similarly, as in the first inlet portion 4, 4' and the second inlet portion 6, 6', another well-known brace bar 21 is provided to the first outlet portion 5, 5' and the second outlet portion 7, 7' so as to be astride the first outlet portion 5, 5' and the second outlet portion 7, 7'. The brace bars 21 are spaced apart from the fixing member 8, 8' by a predetermined distance so as not to come into contact with the fixing member 8, 8'. The arrows in FIGS. 4A through 10D show how the measurement fluid flows.

It goes without saying that various modifications are possible without departing from the scope of the present invention.

The invention claimed is:

1. A Coriolis flowmeter comprising:
   a measurement flow tube including a first curved tube portion and a second curved tube portion, the first curved tube portion having a first inlet portion through which a measurement fluid flows in and a first outlet portion through which the measurement fluid flows out, the second curved tube portion having a second inlet portion through which the measurement fluid flows in and a second outlet portion through which the measurement fluid flows out; and
   a fixing member which is situated in a middle position of the flow tube when looking down at the flow tube, and to which the first inlet portion, the second inlet portion, the first outlet portion, and the second outlet portion are fixed,
   the Coriolis flowmeter being operable to obtain at least one of a mass flow rate and a density of the measurement fluid through detection of at least one of a phase difference and a vibration frequency proportional to Coriolis forces acting on the first curved tube portion and the second curved tube portion by vibrating the first curved tube portion and the second curved tube portion with the first curved tube portion and the second curved tube portion being opposed to each other,
   wherein, the first inlet portion, the second inlet portion, the first outlet portion, and the second outlet portion are fixed to the fixing member such that their tube axes are arranged in the same plane, the first inlet portion and the second inlet portion being arranged in a non-parallel state such that a distance therebetween increases with increasing distance from the fixing member; and the first outlet portion and the second outlet portion being arranged in a non-parallel state such that a distance therebetween increases with increasing distance from the fixing member, the first inlet portion and the second inlet portion, and the first outlet portion and the second outlet portion being fixed so as to be arranged symmetrically, and
   wherein a distance between respective driven portions of the first curved tube portion and the second curved tube portion is smaller than a distance between respective portions thereof continuous with the driven portions.

2. A Coriolis flowmeter according to claim 1, wherein the portions continuous with the driven portion of the first curved tube portion and the first inlet portion and the first outlet portion are arranged in parallel to each other, and the portions continuous with the driven portion of the second curved tube portion and the second inlet portion and the second outlet portion are arranged in parallel to each other.

3. A Coriolis flowmeter according to claim 1, wherein the fixing member is formed substantially in one of a circular configuration and an arcuate configuration when looking down at the flow tube.

4. A Coriolis flowmeter according to claim 3, wherein the fixing member is formed in a wall-like configuration.

5. A Coriolis flowmeter comprising:
   a measurement flow tube including a first curved tube portion and a second curved tube portion, the first curved tube portion having a first inlet portion through which a measurement fluid flows in and a first outlet portion through which the measurement fluid flows out, the second curved tube portion having a second inlet portion through which the measurement fluid flows in and a second outlet portion through which the measurement fluid flows out;
   a fixing member which is situated in a middle position of the flow tube when looking down at the flow tube, and to which the first inlet portion, the second inlet portion, the first outlet portion, and the second outlet portion are fixed; and
   a connecting tube portion provided between the first outlet portion and the second inlet portion and connecting the first outlet portion and the second inlet portion to each other,
   the Coriolis flowmeter being operable to obtain at least one of a mass flow rate and a density of the measurement fluid through detection of at least one of a phase difference and a vibration frequency proportional to Coriolis forces acting on the first curved tube portion and the second curved tube portion by vibrating the first curved tube portion and the second curved tube portion with the first curved tube portion and the second curved tube portion being opposed to each other,
   wherein the first inlet portion, the second inlet portion, the first outlet portion, and the second outlet portion are fixed to the fixing member such that the first inlet portion and the second inlet portion are arranged in a non-parallel state such that a distance therebetween increases with increasing distance from the fixing member; and the first outlet portion and the second outlet portion being arranged in a non-parallel state such that a distance therebetween increases with increasing distance from the fixing member, the first inlet portion and the second inlet portion, and the first outlet portion and the second outlet portion being arranged symmetrically,
   wherein the first outlet portion, the second inlet portion, and the connecting tube portion are arranged such that their tube axes are in a straight line, and
   wherein a distance between respective driven portions of the first curved tube portion and the second curved tube portion is smaller than a distance between respective portions thereof continuous with the driven portions.

6. A Coriolis flowmeter according to claim 5, wherein the portions continuous with the driven portion of the first curved tube portion and the first inlet portion and the first outlet portion are arranged in parallel to each other, and the portions continuous with the driven portion of the second curved tube portion and the second inlet portion and the second outlet portion are arranged in parallel to each other.

7. A Coriolis flowmeter according to claim 5, wherein the fixing member is formed substantially in one of a circular configuration and an arcuate configuration when looking down at the flow tube.

* * * * *